United States Patent [19]

Persson

[11] Patent Number: 5,314,470
[45] Date of Patent: May 24, 1994

[54] VOICE PROSTHESIS

[75] Inventor: Jan-Ove Persson, Höör, Sweden

[73] Assignee: Atos Medical AB, Horby, Sweden

[21] Appl. No.: 866,176

[22] PCT Filed: Dec. 27, 1990

[86] PCT No.: PCT/SE90/00878
§ 371 Date: Jun. 26, 1992
§ 102(e) Date: Jun. 26, 1992

[87] PCT Pub. No.: WO91/09576
PCT Pub. Date: Jul. 11, 1991

[30] Foreign Application Priority Data

Dec. 27, 1989 [SE] Sweden ................. 8904365

[51] Int. Cl.⁵ ................. A61F 2/20; A61F 2/02; A61F 2/04
[52] U.S. Cl. ................. 623/9; 623/11; 623/12
[58] Field of Search ................. 623/12, 11, 66, 9; 128/200.26, 207.12, 207.14, 207.15, 207.16, 207.29

[56] References Cited

U.S. PATENT DOCUMENTS

| | | | |
|---|---|---|---|
| 4,435,853 | 3/1984 | Blom et al. | 623/9 |
| 4,610,691 | 9/1986 | Depel et al. | 623/9 |
| 4,808,183 | 2/1989 | Panje | 623/9 |
| 5,064,433 | 11/1991 | Blom et al. | 623/9 |

FOREIGN PATENT DOCUMENTS 0222509  5/1987  European Pat. Off. .
2494581  5/1982  France .

Primary Examiner—Randall L. Green
Assistant Examiner—Dinh X. Nguyen
Attorney, Agent, or Firm—Bell, Seltzer, Park & Gibson

[57] ABSTRACT

A voice prosthesis is adapted to be inserted into a fistula between an esophagus and a trachea of a user. This prosthesis includes a cylindrical middle piece defining a passageway therethrough which has a groove therein and which has first and second end portions. First and second external flanges extend from respective first and second end portions of the middle piece. The middle piece and the flanges are all made of flexible material. A ring made of a material which is stiff in relation to the flexible material of the middle piece and the flanges is inserted into the groove in the passageway of the middle piece for stiffening of the middle piece. A valve is provided which includes a seat formed in the passageway of the middle piece and a flap extending across the passageway and carried by the middle piece for resting on the seat to close the passageway and is adapted to be moved off the seat to open the passageway.

5 Claims, 1 Drawing Sheet

VOICE PROSTHESIS

BACKGROUND AND OBJECTS OF THE INVENTION

The invention relates to a voice prosthesis.

As a result of different diseases the larynx of the diseased must sometimes be removed in an operation. In connection with such operations there must also be made a so called tracheostoma or an artificial tracheostoma fistula into the trachea so as to make possible breathing. Food stuff is taken in through the esophagus which is completely separated from the trachea.

Due to the measures mentioned above the ability of speech is lost. To some extent restore the ability of speech it is possible, by means of an operation, to open a fistula between the esophagus and the trachea to direct air to the oral cavity. However, said fistula must always be closed, except when air is admitted into the pharynx, because food stuff and liquids must be prevented from entering the trachea and further into the lungs.

To make it possible to open and close said fistula a so called voice prosthesis functioning as a one-way valve is inserted in said fistula. Said one-way valve permits air to pass from the trachea to the esophagus when a certain opening pressure has been reached in the trachea, but has to be completely closed in the reverse direction.

A voice prosthesis of this type is disclosed in U.S. Pat. No. 4,610,691. Said voice prosthesis includes a cylindrical housing having an inlet opening and an outlet opening and is mounted in such a way that said inlet opening opens into the trachea and said outlet opening opens into said esophagus. Said outlet opening is provided with a one-way valve in form of a perpendicular membrane hingedly mounted within the housing. Throughout the complete housing is a boring which at the point where said membrane is hinched is provided with a radially extending rim functioning as a sealing structure to said membrane. The inner diameter of said boring is substantially reduced at the position of said rim resulting in a decreased flow capacity of said prosthesis. The chosen type of valve results in a low opening pressure but the assembling of said prosthesis is complicated and the requirements for assembling are very high to minimize the risk that said membrane falls off, and also to insure that said membrane seals completely against said sealing structure.

A different form of voice prosthesis is put on the market by ENTERMED, P O Box 236, 3440 AI Woerden Hollland. Said prosthesis comprises a cylindrical web having an annular external flange in one end and a circular end wall formed with a slit in the other end. Said end wall extends radially from said web as an external flange and is curved in a convex shape. Said slit functioning as a valve extends as a diameter over said end wall and is normally closed. The prosthesis is inserted with said flange in trachea and said end wall in esophagus. In this type of voice prosthesis a very high opening pressure is required, and furthermore said valve is sensitive to influence from muscular movements in the esophagus, for instance at swallowing.

An object of the present invention is to overcome substantially the drawbacks and deficiencies of previously known voice prosthesis and to ensure a secure one-way function while maintaining a low opening pressure. Furthermore, the voice prosthesis according to the invention is comparatively easy to manufacture and to insert in the throat, and also permits a high flow in relation to the outer dimensions thereof. According to a further development a voice prosthesis has been accomplished which when mounted has a low tendency of rotating.

BRIEF DESCRIPTION OF THE DRAWINGS

The invention will now be described in more detail by means of an embodiment, reference being made to the accompanying drawings, in which.

DETAILED DESCRIPTION OF PREFERRED EMBODIMENT OF THE INVENTION

Figure 1:
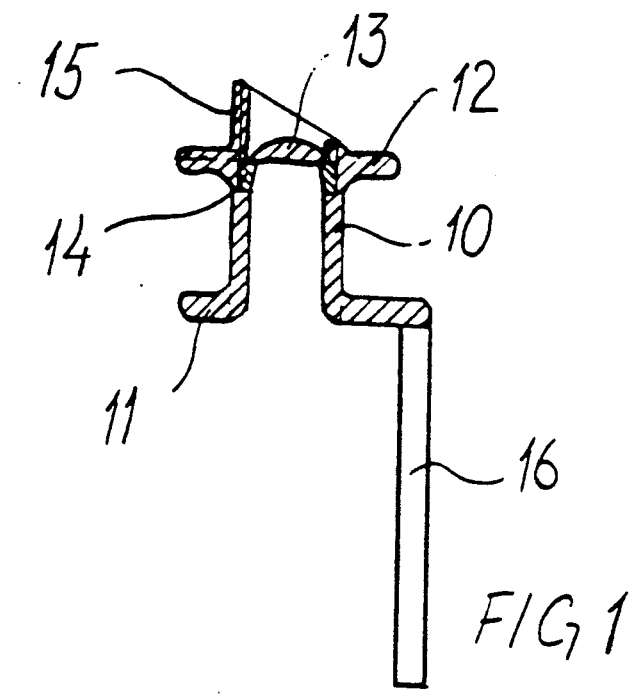
FIG. 1 is a longitudinal sectional view of a device according to the invention.

The voice prosthesis shown in FIG. 1 comprises a cylindrical middle piece 10, a first end thereof being provided with a first extending external annular flange 12. Said first flange 12 is intended to engage the inside of the esophagus after insertion in the throat. The second end of said middle piece 10 is provided with a second external flange 11. Said second, somewhat oval-shaped annular flange 11 is intended to engage the inside of the trachea after insertion in the throat. Said flange 11 and a tail 16 attached to one end of said flange and extending in a direction from said middle piece 10 is described in more detail below with reference to FIG. 2.

Said middle piece 10 is radially within said first flange 12 provided with a circular valve flap 13 which is integrated with said middle piece. Said valve flap 13 is along the major part of the periphery thereof cut free from said middle piece leaving a shorter peripheral section constituting the link of said valve flap. Said valve flap is made comparatively thin and said link has a very low flexural resistance and a very low pressure is required to open said valve. An obliqually cut cylindrical section 15 constitutes an extension of the cylindrical middle piece 10 beyond said first flange 12. In the embodiment shown said link is arranged at the section 15 of the extension of said middle piece which is mostly cut, but the link can be disposed also in other positions. Said section 15 protects the sensitive valve flap from external influence. All parts of the prosthesis described above are in the shown embodiment made of silicon. Also other flexible materials can be used.

Axially within said valve flap an internal groove is made in said middle piece 10, and a stiffening ring 14 is inserted in said groove. Said ring is made of a material which in relation to other parts of said prosthesis is hard, and in the shown embodiment rigid plastic is used, and the inner diameter of said ring is chosen so as to make the inner periphery of said ring an extension of the inner periphery of said middle piece. Thus the inner diameter is substantially constant thoughout the entire length of said prosthesis. In the embodiment shown one annular end section of said ring is the seat for said valve flap 13. However, the stiffening functioning of said ring can be used also if said internal groove is somewhat indented into said middle piece and a section of said middle piece is arranged as a valve seat. Thanks to the stiffening of the prosthesis the sensitivity of the valve for muscular movements in surrounding muscles, for instance at swallowing is substantially reduced. As a result of the low sensitivity the risk that for instance liquid passes through said valve in the back flow direction is decreased.

Figure 2:
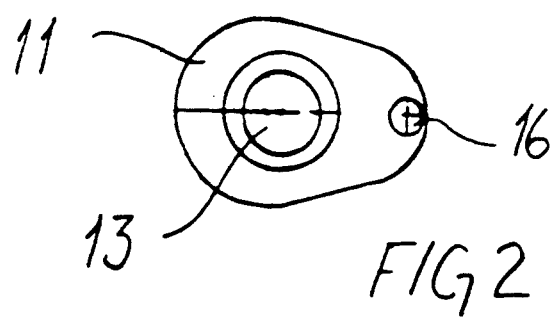
FIG. 2 is a view from below of the device according to FIG. 1.

From FIG. 2 the oval or egg shape of said flange 11 and the positioning of said tail in a section of said flange 11 extending from the middle piece are clear. Said tail 16 is used when said prosthesis is inserted in the throat of the patient and is removed from the prosthesis after insertion. The oval shape of said flange facilitates substantially the insertion. Also risks for damages on the fistula during insertion are substantially decreased. Furthermore, the oval shape prevents, substantially completely, that the prosthesis rotates around the central axes thereof after insertion. With a circular flange 11 the risk of rotation is substantially larger. If the prosthesis may rotate some of the protective properties of said section 15 is lost. Instead of a tail 16 which is permanently connected to the flange 11, the prosthesis can be provided with a removable portion, such as a hook and cord, which are used during insertion of the prosthesis.

I claim:

1. A voice prosthesis adapted to be inserted in a fistula between an esophagus and a trachea of a user, said prosthesis comprising:
    a cylindrical middle piece defining a passageway therethrough which has a groove therein and having first and second end portions;
    a first external flange extending from said first end portion of said middle piece;
    a second external flange extending from said second end portion of said middle piece;
    said middle piece and said first and second flanges being made of flexible material;
    a ring made of a material which is stiff in relation to the flexible material of said middle piece and said first and second flanges and inserted into said groove in said passageway of said middle piece for stiffening said middle piece; and
    valve means including a seat formed in said passageway of said middle piece and a flap extending across said passageway and carried by said middle piece for resting on said seat to close said passageway and being adapted to be moved off said seat to open said passageway.

2. A voice prosthesis, as set forth in claim 1, in which said flap is connected with and is integral with said middle piece.

3. A voice prosthesis, as set forth in claim 1 or 7, in which said ring forms said seat of said valve means.

4. A voice prosthesis, as set forth in claim 1 or 2, in which said second flange is flat and oval shaped defining an annular section and a tapered section extending therefrom, and further including a longitudinally-extending portion connected to and extending from said tapered section in a direction away from and axially of said middle piece.

5. A voice prosthesis, as set forth in claim 4, in which said longitudinally-extending portion is removably connected to said second flange.

* * * * *

UNITED STATES PATENT AND TRADEMARK OFFICE
CERTIFICATE OF CORRECTION

PATENT NO. : 5,314,470
DATED : May 24, 1994
INVENTOR(S) : Jan-Ove Persson

It is certified that error appears in the above-identified patent and that said Letters Patent is hereby corrected as shown below:

IN THE CLAIMS:

Column 4, line 19, "7" should be -- 2 --.

Signed and Sealed this

Thirtieth Day of August, 1994

Attest:

BRUCE LEHMAN

*Attesting Officer*     *Commissioner of Patents and Trademarks*